US006462229B1

(12) United States Patent
Meul

(10) Patent No.: US 6,462,229 B1
(45) Date of Patent: Oct. 8, 2002

(54) PROCESS FOR THE PREPARATION OF (-)-α-(DIFLUOROMETHYL)ORNITHINE-MONOHYDROCHLORIDE MONOHYDRATE

(75) Inventor: Thomas Meul, Visp (CH)

(73) Assignee: Lonza Ltd. (CH)

( * ) Notice: Subject to any disclaimer, the term of this patent is extended or adjusted under 35 U.S.C. 154(b) by 0 days.

(21) Appl. No.: 09/787,420

(22) PCT Filed: Sep. 22, 1999

(86) PCT No.: PCT/EP99/07060

§ 371 (c)(1),
(2), (4) Date: Jul. 20, 2001

(87) PCT Pub. No.: WO00/17153

PCT Pub. Date: Mar. 30, 2000

(30) Foreign Application Priority Data

Sep. 23, 1998 (EP) .............................. 98117982

(51) Int. Cl.⁷ .................. C07B 57/00; C07C 53/00; C07C 205/00; C07C 229/00
(52) U.S. Cl. .................. 562/402; 562/512; 562/553; 562/561
(58) Field of Search ............... 562/561, 402, 562/512, 553

(56) References Cited

U.S. PATENT DOCUMENTS 4,309,442 A * 1/1982 Bey et al.
4,414,141 A 11/1983 Bey et al.

FOREIGN PATENT DOCUMENTS

| EP | 0 365 213 | | 10/1989 |
| EP | A20365213 | * | 4/1990 |
| WO | WO 98/14188 | * | 4/1998 |
| WO | WO 98/25603 | | 6/1998 |

OTHER PUBLICATIONS

F.J. Kearley & A.W. Ingersol, *The Resolution of Amino Acids. IV. Lysine*, Dec. 1951, pp. 5783 to 5785.

Journal of the American Chemical Society; David A. Jaegar, Michael D. Broadhurst, and Donald J. Cram, Jan. 31, 1979; pp. 717 to 732.

Tetrahedron Letters, vol. 38, No. 34, pp. 5965–5966, 1997.

J. Jacques et al., John Wiley & Sons, (1981), pp. 261–263.

* cited by examiner

*Primary Examiner*—Alan L. Rotman
*Assistant Examiner*—Héctor M Reyes
(74) *Attorney, Agent, or Firm*—Fisher, Christen & Sabol

(57) ABSTRACT (±)-α-(Difluoromethyl)-ornithine is separate into its isomers using (−)-O,O'-di-p-toluoyl-L-tartaric acid. (−)-α-(Difluoromethyl)-ornithine monohydrochloride monohydrate and in particular the (−)-isomer are inhibitors of ornithine decarboxylase and thereby have numerous pharmacological actions.

15 Claims, No Drawings

PROCESS FOR THE PREPARATION OF (-)-α-(DIFLUOROMETHYL)ORNITHINE-MONOHYDROCHLORIDE MONOHYDRATE

This application is a 371 national stage application of PCT/EP99/07060, filed on Sep. 22, 1999, which has benefit of priority of European Application 98117982.3, filed on Sep. 23, 1998.

BACKGROUND OF THE INVENTION

1. Field of the Invention

The present invention relates to a process for the resolution of (±)-α-difluoromethylornithine of the formula:

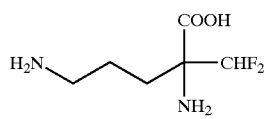

I using (-)-O,O'-di-p-toluoyl-L-tartaric acid. (±)-α-Difluoromethylornithine is an inhibitor of ornithine decarboxylase and has numerous pharmacological actions (U.S. Pat. No. 4,413,141).

2. Background Art

It is known that the pharmacological activity of the (-)-isomer is significantly greater than that of the racemate (WO-A-98/25603).

The known methods for the preparation of the (-)-isomer, however, are laborious and unsatisfactory with respect to the yield and optical purity which can be achieved.

According to U.S. Pat. No. 4,413,141 or U.S. Pat. No. 4,309,442, for the purpose of resolution, DL-3-amino-3-difluoromethyl-2-piperidone of the formula:

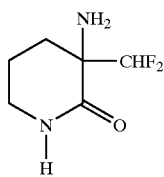

II is used, which first has to be prepared from racemric DL-α-difluoromethylornithine monohydrochloride monohydrate via formation of the methyl ester and cyclization using alkoxide. The resolution of the piperidonie is described using classical resolving agents such as, for example, using (+)-camphor-10-sulphonic acid or using (+)- or (-)-binaphthyl-phosphoric acid.

BROAD DESCRIPTION OF THE INVENTION

The object of the invention consisted in developing an approach to the desired isomer which was simpler and improved with respect to yield and optical purity.

It has been found that (±)-α-difluoromethylornithine can be cleaved using the commercially obtainable (-)-O,O'-di-p-toluoyl-L-tartaric acid, without circuitous routes and without having to take the disadvantages mentioned into account, and consequently it was thus possible to achieve the object in a surprisingly simple manner.

The invention therefore relates to diastereomeric salts of (+)- or (-)-α-difluoromethylornithine of the formula:

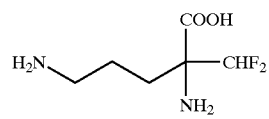

I with (-)-O,O'-di-p-toluoyl-L-tartaric acid, preferably the 1:1 diastereomeric salt of (+)- or (-)-α-difluoromethylornithine with (-)-O,O'-di-p-toluoyl-L-tartaric acid and particularly preferably the 1:1 diastereomeric salt of (-)-α-difluoromethylornithine with (-)-O,O'-di-p-toluoyl-L-tartaric acid.

In the preferred molar ratio of resolving agent to (-)-α-difluoromethylornithine of 1:1, in principle two free amino groups are available for bonding. Fundamentally, both diastereomers are included by the invention.

A further subject of the invention is the process according to the invention. The invention process involves resolution of (±)-α-(difluoromethyl)-ornithine of formula I. The resolution is carried out using (-)-O,O'-di-p-toluoyl-L-tartaric acid.

DETAILED DESCRIPTION OF THE INVENTION

The resolution of (±)-α-difluoromethylornithine using (-)-O,O'-di-p-toluoyl-L-tartaric acid is expediently carried out in the presence of a mixture of water and a water-miscible polar organic solvent.

Suitable water-miscible polar organic solvents are, for example, lower aliphatic alcohols, such as methanol or ethanol, or acetonitrile. A preferred water-miscible polar organic solvent is acetonitrile.

The components are expediently dissolved by heating. On cooling, as a rule the desired diastereomer of (-)-α-difluoromethylornithine with (-)-O,O'-di-p-toluoyl-L-tartaric acid crystallizes out, while the diastereomer of (+)-α-difluoromethylornithine with (-)-O,O'-di-p-toluoyl-L-tartaric acid remains in solution.

Customarily, the mixture water/water-miscible polar organic solvent is selected such that the desired diastereomer of (-)-α-difluoromethylornithine with (-)-O,O'-di-p-toluoyl-L-tartaric acid crystallizes out easily and quantitatively on cooling the solution.

Preferably, a mixture of acetonitrile/water of 0.9:1 to 1.3:1 is selected for the crystallization of the 1:1 diastereomer of (-)-α-difluoromethylornithine with (-)-O,O'-di-p-toluoyl-L-tartaric acid.

The liberation of the (-)-α-difluoromethylornithine monohydrochloride monohydrate from the diastereomer is carried out by acidifying with a mineral acid such as, with hydrochloric acid. By extraction with a suitable solvent, the (-)-α-difluoromethylornithine monohydrochloride monohydrate can be obtained in high yield and high optical purity. The (-)-O,O'-di-p-toluoyl-L-tartaric acid can likewise be recovered from this extraction.

The diastereomer of (+)-α-difluoromethylornithine with (-)-di-O,O'-p-toluoyl-L-tartaric acid, which as a rule is found in solution, can likewise be analogously liberated, e.g. after evaporation of the solution, as (+)-α-difluoromethylornithine monohydrochloride monohydrate, which can then be recovered by extraction, by acidifying with a mineral acid.

EXAMPLE 1

Preparation of (−)-α-difluoromethylornithine.HCl.H$_2$O 91 g of (±)-α-difluoromethylornithine and 19.7 g (−)-O,O'-di-p-toluoyl-L-tartaric acid were introduced into a mixture of 150 ml of acetonitrile and 110 ml of water and heated to boiling, a clear solution resulting. On cooling, the diastereomeric 1:1 salt of (−)-α-difluoromethylornithine and (−)-O,O'-di-p-toluoyl-L-tartaric acid crystallized out at 47 to 48° C. The crystallization was completed by cooling to 5° C. to 0° C. The crystallized salt was filtered off and dried. 9.7 g of white crystalline product were obtained. $[\alpha]^{20}_D = -99.1°$ (c=1 in MeOH)

$^1$H-NMR (400 MHz, DMSO-d$_6$) δ = 7.83 (d, J = 7.7 Hz, 4H)
7.30 (d, J = 7.7 Hz, 4H)
6.21 (t, J = 54 Hz, 1H)
5.63 (s, 2H)
2.77 – 2.66 (m, 2H)
2.36 (s, 6H)
1.87 – 1.46 (m, 4H)

M.p.: 172.9–173.7° C.

8.5 g of this salt were introduced into 100 ml of water and treated with a solution of 1.7 g of concentrated hydrochloric acid (32.2%, strength) in 20 ml of water. The suspension was extracted with 200 ml of chloroform. The aqueous phase was evaporated to dryness. After drying at 40° C. in a vacuum oven overnight, 3.2 g of white product were obtained.

$[\alpha]^{20}_D = -8.8°$ (c=0.7 in MeOH)

EXAMPLE 2

Preparation of (+)-α-difluoromethylornithine.HCl.H$_2$O

From the evaporated mother liquor of the resolution from Example 1, according to the process described above, (+)-α-difluoromethylornithine monohydrochloride monohydrate was isolated with an optical rotation of $[\alpha]^{20}_D = +3.1°$ (c=7.0 in MeOH).

$^1$H-NMR (400 MHz, D$_2$O) δ = 6.30 (t, J = 54 Hz, 1H)
3.01 (m, 2H)
2.05 (m, 1H)
1.89 (m, 1H)
1.85 (m, 1H)
1.62 (m, 1H)

What is claimed is:

1. A salt of S-(+)- or R-(−)-α-(difluoromethyl)ornithine, the R-(−)-α-(difluoromethyl)ornithine represented by the formula:

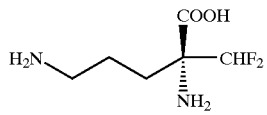

and the S-(+)-α-(difluoromethyl)ornithine represented by the formula:

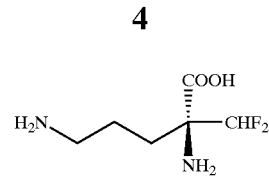

with (−)-O,O'-di-p-toluoyl-L-tartaric acid.

2. 1:1 salt of R-(−)-α-(difluoromethyl)ornithine with (−)-O,O'-di-p-toluoyl-L-tartaric acid.

3. 1:1 salt of S-(+)-α-(difluoromethyl)ornithine with (−)-O,O'-di-p-toluoyl-L-tartaric acid.

4. A process for the resolution of [S-(+)/R-(−)]-α-(difluoromethyl)ornithine, the R-(−)-α-(difluoromethyl)ornithine represented by the formula:

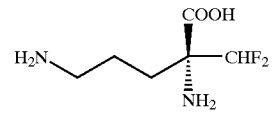

and the S-(+)-α-(difluoromethyl)ornithine represented by the formula:

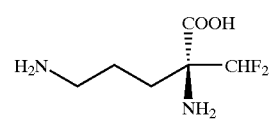

comprising conducting the resolution using (−)-O,O'-di-p-toluoyl-L-tartaric acid.

5. The process according to claim 4, wherein the process is carried out in the presence of a mixture of water and a water-miscible polar organic solvent.

6. The process according to claim 5, wherein acetonitrile is used as the water-miscible polar organic solvent.

7. The process according to claim 6, wherein volume ratio of acetonitrile to water is 0.9:1 to 1.3:1 in the mixture of acetonitrile and water.

8. The process according to claim 5, wherein the water-miscible polar organic solvent is a lower aliphatic alcohol.

9. The process according to claim 5, wherein acetonitrile is used as the water-miscible polar organic solvent.

10. The process according to claim 6, wherein 1:1 salt of R-(−)-α-(difluoromethyl)ornithine with (−)-O,O'-di-p-toluoyl-L-tartaric acid is crystallized out and R-(−)-α-(difluoromethyl)ornithine monohydrochloride monohydrate is liberated by acidification.

11. The process according to claim 10, wherein the acidification is carried out using a mineral acid.

12. The process according to claim 11, wherein the mineral acid is hydrochloric acid.

13. The process according to claim 4, wherein 1:1 salt of R-(−)-α-(difluoromethyl)ornithine with (−)-O,O'-di-p-toluoyl-L-tartaric acid is crystallized out and R-(−)-α-(difluoromethyl)ornithine monohydrochloride monohydrate is liberated by acidification.

14. The process according to claim 13, wherein the acidification is carried out using a mineral acid.

15. The process according to claim 14, wherein the mineral acid is hydrochloric acid.

* * * * *